(12) United States Patent
Schwarz et al.

(10) Patent No.: US 9,119,638 B2
(45) Date of Patent: Sep. 1, 2015

(54) DEVICE AND METHOD FOR TREATING PARTS OF A HUMAN OR ANIMAL BODY

(76) Inventors: Markus Schwarz, Ebenhausen (DE); Peter Pott, Mannheim (DE)

(*) Notice: Subject to any disclaimer, the term of this patent is extended or adjusted under 35 U.S.C. 154(b) by 1169 days.

(21) Appl. No.: 11/068,099

(22) Filed: Feb. 28, 2005

(65) Prior Publication Data

US 2005/0171553 A1 Aug. 4, 2005

Related U.S. Application Data

(63) Continuation of application No. PCT/DE03/02846, filed on Aug. 25, 2003.

(30) Foreign Application Priority Data

Aug. 26, 2002 (DE) .................................. 102 39 673

(51) Int. Cl.
*A61B 17/16* (2006.01)
*A61B 19/00* (2006.01)
*A61B 17/17* (2006.01)
(Continued)

(52) U.S. Cl.
CPC ......... *A61B 17/1626* (2013.01); *A61B 19/5244* (2013.01); *A61B 17/1757* (2013.01); *A61B 19/22* (2013.01); *A61B 19/5212* (2013.01); *A61B 2019/5265* (2013.01); *G01S 5/02* (2013.01); *G01S 5/16* (2013.01); *G01S 5/18* (2013.01); *G05B 2219/45168* (2013.01)

(58) Field of Classification Search
CPC .................. A61B 17/1626; A61B 2019/2288; A61B 19/5244

USPC ...................................................... 606/96–98
See application file for complete search history.

(56) References Cited

U.S. PATENT DOCUMENTS 2,141,284 A * 12/1938 Woock ............................ 73/859
4,800,802 A 1/1989 Rebman
(Continued)

FOREIGN PATENT DOCUMENTS

DE 196 49 082 C1 11/1996
DE 197 00 402 A1 7/1998
(Continued)

OTHER PUBLICATIONS

D'Attanasio, S., et al. A Semi-Automatic Handheld Mechatronic Endoscope with Collioion-Avoidance Capabilities. Proceedings of the 2000 IEEE. Apr. 2000. pp. 1586-1591.*
(Continued)

*Primary Examiner* — David Bates
(74) *Attorney, Agent, or Firm* — Alston & Bird LLP

(57) ABSTRACT

A device and method for treating all types of parts, in particular bones, organs, etc. of the human/animal body, which includes a housing (3), a tool (1) associated with the housing (3), and an actuation unit causing a relative movement between the housing and the tool. The device is designed and constructed to permit process control by the user, while utilizing the specific possibilities of robotics and computer-assisted navigation in such a manner that the position of the tool can be detected, and that the position of the body part being treated can be detected or predetermined, with the actuation unit being activatable in such a manner that it moves the tool within a predetermined work area to a predetermined relative position with respect to the body part being treated.

21 Claims, 3 Drawing Sheets

(51) Int. Cl.
G01S 5/02 (2010.01)
G01S 5/16 (2006.01)
G01S 5/18 (2006.01)

(56) References Cited

U.S. PATENT DOCUMENTS

| | | | |
|---|---|---|---|
| 5,458,206 A * | 10/1995 | Bourner et al. | 173/178 |
| 5,688,118 A | 11/1997 | Hayka et al. | |
| 6,000,939 A | 12/1999 | Ray et al. | |
| 6,043,621 A * | 3/2000 | Neumann | 318/568.11 |
| 6,238,384 B1 * | 5/2001 | Peer | 606/1 |
| 6,450,978 B1 * | 9/2002 | Brosseau et al. | 600/595 |
| 6,519,860 B1 * | 2/2003 | Bieg et al. | 33/503 |
| 6,554,837 B1 | 4/2003 | Hauri et al. | |
| 7,811,294 B2 * | 10/2010 | Strommer et al. | 606/108 |
| 2001/0012932 A1 | 8/2001 | Peer | |
| 2003/0026703 A1 | 2/2003 | Yoo et al. | |
| 2004/0077939 A1 | 4/2004 | Graumann | |
| 2004/0157188 A1 | 8/2004 | Luth et al. | |
| 2012/0143084 A1 * | 6/2012 | Shoham | 600/567 |
| 2013/0060278 A1 * | 3/2013 | Bozung et al. | 606/205 |

FOREIGN PATENT DOCUMENTS

| | | |
|---|---|---|
| DE | 199 02 273 A1 | 8/2000 |
| DE | 100 45 779 A1 | 2/2002 |
| DE | 102 25 007 | 2/2003 |
| EP | 0 456 103 A2 | 11/1991 |
| WO | WO 97/30826 A1 | 8/1997 |

OTHER PUBLICATIONS

D'Attanasio et al. A Semi-Automatic Handheld Mechatronic Endoscope with Collision-Avoidance Capabilities. Apr. 2000. Proceedings of the IEEE, 2000.*

*A Semi-Automatic Handheld Mechatronic Endoscope With Collision-Avoidance Capabilities*, S. D'Attanasio et al., Proceeding of the 2000 IEEE, International Conference on Robotics & Automation, San Francisco, CA, Apr. 2000, pp. 1586-1591.

*Acrobot: A "Hands-on" Robot for Total Knee Replacement Surgery*, M. Jakopec et al., 2002 IEEE, pp. 116-120.

*Design and Implementation of Active Error Canceling in Hand-held Microsurgical Instrument*, W. T. Ang et al., Proceedings of the 2001 IEEE/RSJ International Conference on Intelligent Robots and Systems, Maui, Hawaii, Oct.-Nov. 2001, pp. 1105-1111.

* cited by examiner

DEVICE AND METHOD FOR TREATING PARTS OF A HUMAN OR ANIMAL BODY

CROSS REFERENCE TO RELATED APPLICATION

The present application is a continuation of international application PCT/DE2003/002846, filed 25 Aug., 2003, and which designates the U.S. The disclosure of the referenced application is incorporated herein by reference.

BACKGROUND OF THE INVENTION

The present invention relates to a device and method for treating all types of parts, in particular bones, organs, etc. of the human/animal body, and which includes a housing, a tool associated to the housing, and an actuation unit that causes a relative movement between the housing and the tool.

For a surgical manipulation of bones, in particular in orthopedic surgery, it has already become common practice to use passive navigators, which assist a user in the orientation of the tool on the patient and in a precise operative planning of the surgery. However, all operational steps are performed by the users themselves.

In these navigation systems, the computer navigated tools do not automatically reach the desired position, because they are opposed by muscle tremor and involuntary transient movements of the operator during the operation. Accordingly, the pre-operative planning is put into action with imperfections.

In particular in the case of endoprothesis of the hip and knee as well as corrective surgery of the hip joint and replacement of the anterior cruciate ligament of the knee, it is common to use robots, which automatically perform as active navigators on the patient surgical steps that may be previously programmed at a work station or directly in the operating room.

A disadvantage of such systems is on the one hand the prolonged duration of the operation, and on the other hand the very high costs of purchase and upkeep as well as the additional floor space requirements for such systems. Moreover, when using a robot, many surgeons subjectively miss a process control by reason of events which may occur on the operating table.

A device of the generic type is disclosed in DE 197 00 402 C2. The appliance described therein makes it possible to compensate to the greatest extent possible involuntarily occurring trembling of the hands (tremor), when manually working on fine structures. This compensation of the muscle tremor is of great importance in particular in microsurgery. In this connection, the appliance mounts acceleration and angular speed sensors that supply a mechanical or electrical signal which correlates with the movement of the appliance. These sensor signals are amplified in a first step. Subsequently, they are analyzed with respect to frequency, amplitude, and direction or acceleration of the tool. It is thus possible to evaluate undesired movements and differentiate them from intended movements. With reference to the data, it is possible to activate the actuators such that they cause relative movements of the movable section for compensating an undesired deflection of the handheld section.

While the known device permits excluding the muscle tremor from the tool movement to a large extent, it is problematic in that positioning of the tool cannot be controlled in a programmable fashion, but must be performed by hand. When a surgeon applies the operating tool, for example, a drill, in a wrong location or in a wrong angular position, the known device will not detect this error, and consequently will not correct it.

It is therefore an object of the present invention to provide a device and method of the initially described type for treating all types of body parts, in particular bones, organs, etc. of the human/animal body, which allows the user significant control over the process and a rapid and reliable work routine, while making use of specific possibilities of robotics and computer assisted navigation.

SUMMARY OF THE INVENTION

The above and other objects and advantages of the invention are achieved by the provision of a device and method which comprises a housing, a tool mounted for movement within the housing, and an activation unit for causing relative movement between the tool and the housing.

The device of the invention is constructed such that the position of the tool is detectable, and the position of the part being treated is detectable or predetermined. In this process, it is possible to activate the actuation unit such that it moves the tool within a predetermined work area to a predetermined relative position with respect to the body part being treated.

To begin with, it has been recognized by the invention that despite muscle tremor and other unavoidable wrong movements of the user, it is also possible to attain with a handheld appliance a mechanical precision in the treatment of all types of body parts, in particular in microsurgical operations, as are already known from procedures which utilize robots as active or semiactive navigators.

To this end, the invention provides for detecting in a first step the positions of the tool and the body part being treated. In a next step, the detected position data are compared with predetermined position data. By means of a measured deviation, the actuation unit is activated, which moves the tool to a predetermined relative position with respect to the part being treated. In this process, the actuation unit causes the tool to move relative to a housing held by the user, so that in accordance with the invention the predetermined positioning of the tool is achieved, within a certain work area, independently of the movements of the user and independently of the movements of the body part being treated. Reaction movements of the user, which are caused by the treatment process because of a mechanical feedback between the tool and the hand of the user, are corrected during the entire treatment process. The handheld use allows the operator a greater process control than known robot systems.

Advantageously, the device comprises an adaptive and quick acting controller unit. The latter evaluates the detected position data in a first step, and subsequently generates the controlled variables for the actuation unit. These two procedures, i.e. detecting the positions of the tool and the part being treated, as well as activating the actuation unit, are preferably performed continuously or repetitively. With that, it becomes possible to detect and correspondingly correct also fast or high frequency movements of the tool, which for example are caused by the muscle tremor of the surgeon as well as the movements of the body parts being treated which may result from trembling of the patient.

The tool could be movable relative to the housing in all six degrees of freedom. The degrees of freedom consist of displacements along the three Cartesian axes (x, y, z), wherein a displacement along the z axis constitutes the advance of the tool. To compensate for incorrect angular positions of the tool, it would also be possible to make the angle of inclination $\alpha$ and the yaw angle $\psi$ variable relative to the housing. The sixth degree of freedom is the rotation of the tool about the z-axis, which corresponds to the actual rotation of the drill.

The housing which is designed to be handheld by the user during the procedure could be constructed to include a handle, pistol grip, or the like. This configuration results in an excellent operability of the appliance, which means for the user a maximum of control over the operating procedure.

To detect the position data of the tool and the part being treated, it is possible to provide an external position finding system, which could advantageously operate with optical, and/or acoustical, magnetic, mechanical, or radioactive signals. The application DE 102 25 007.4, the disclosure of which is incorporated herein by reference, discloses the following with respect to optical tracking systems:

The use of more than two optical sensors permits introducing redundancy into tracking systems, which is usable among other things, but not only, for increasing tracking accuracy, tracking speed, and tracking ruggedness. For example, it is possible to calibrate a moved sensor with the use of data from momentarily unmoved sensors.

Furthermore, the use of passive or active color markings on the objects being tracked permits differentiating the different markers, which leads, among other things, to an increase of the tracking speed.

Image processing, which arises in the case of optical tracking can be clearly accelerated with the use of special hardware, for example field programmable gate arrays (FPGAs). A preferred variant of such a setup permits associating a corresponding hardware to each image sensor. A possibly existing host or control system is relieved in part or in full by the use of, for example, FPGA hardware.

Thus, a large, flexible, and unshadowed operating field is available to the user, which permits working without changing the ambient field or routine of the operation.

For an easier identification of the objects being tracked, i.e. the tool and body part being treated, same could advantageously be provided with markings that are detected by the tracking system. Within the scope of operational planning, it is possible to align the actual position of the marker arranged on the bone being treated with a presurgical CT of the patient. In this process, at least three spaced markers could be associated to the tool, which permits not only detecting the position, for example, of the tool bit, but also determining the orientation of the tool in the space.

Since a marker arranged on the tool bit is optically no longer accessible after the tool enters the body part being treated, it would be possible and very advantageous to associate to the housing a detectable marker. Furthermore, one could provide an inner sensor that is associated directly or indirectly to the housing and/or the tool, and is used to determine the relative position between the housing and the tool. In a preferred manner, one could use for this purpose mechanical displacement sensors or angle sensors. This indirect determination of the position of the tool ensures the functioning of the device during the entire operation, in particular also after the tool bit has entered the body part being treated.

To position the tool, the actuation unit could comprise actuators, which could apply in the predetermined work area of the tool static and/or dynamic forces in each spatial direction. The use of actuators is intended to correct false positionings of the tool by the operator as well as position deviations during the operating procedure (for example, the drill "running off center" in the bone). It would be possible to monitor all occurring forces and moments during the entire operational procedure. In this manner, it would then be possible to register, for example, also jerky movements of great amplitude ("jerking"). In this case, the tool could automatically disconnect upon occurrence of such a movement.

The technical realization of the actuation unit could be provided in an advantageous manner by a hexapod (Steward and flight simulator platform). This hexapod could be formed in particular by very small and highly dynamic linear motors, so that it would be possible to realize a unit of a corresponding overall size. This unit could be easily integrated into the handheld housing. The hexapod offers the possibility of performing movements in all six degrees of freedom in a work area that is adequately large for the application.

In an alternative realization, the actuation unit could have a construction, which is based on the parallel arrangement of two epicyclical gear trains. With a merely rotational actuation, this would enable a movement of the drill shaft in four degrees of freedom, namely displacements in the x and y directions, as well as rotations about the x and y axis. The movements can be performed very precisely, rapidly, and in a space saving manner as a result of the small number of components and the favorable arrangement.

Basically, there are no limits to the configuration of the tool. Possible in medical applications are, for example, drills, milling cutters for milling cavities in bones, or also forceps for use during a biopsy. At this point, it should again be emphasized that the use of the device according to the invention is not limited to medical, in particular surgical procedures, but that it also permits performing precision cutting, machining, sawing, or similar operations in the field of automated industrial production and/or do-it-yourself projects.

With respect to a mobility of the tool that is adequate as regards vibrations or shaking movements of the user's hand, it could be provided that in a special realization, the tool has a cylindrical work area of about 40 mm diameter and about 40 mm length. This would approximately correspond to an angular mobility of the tool of ±20° in the zx and zy planes.

Within the work area, the accuracy in the position control of the tool could be in a special realization so high that the tool bit is always located in a defined manner in a cube of 0.1 mm edge length. The alignment of the tool should not deviate more than 0.10 from the ideal direction.

In particular for the use of the tool in the operating room area, it could be provided that both the tool and the housing can be sterilized. As regards a user friendly operation of the device, it could be provided that the operating procedure, for example, the drilling step is initially blocked. Only after the operator has moved the appliance in the vicinity of the planned drilling position, and after the actuation unit has correctly aligned the drill in its angular position and in its position, will the drilling procedure be automatically released. This could be indicated, for example, by an acoustic and/or optical signal.

During the operation, it would be possible to monitor certain working parameters automatically. In the case of a drilling procedure, one has in mind in particular the rate of advance, the force of advance, as well as the rotational speed of the drill. After reaching the planned drilling depth, it would be possible to provide for an automatic disconnection of the drill.

Advantageously, the position finding system has a sampling rate of at least 50 Hz. This frequency is necessary to be able to also detect rapid movements or higher frequency vibrations, which are in the range of about 12 Hz in the case of muscle tremor. The system could be designed such that a total of six markers can be detected at a sampling rate of 50 Hz. As regards accuracy in determining a position, the position finding system could be designed such that the error is smaller than 0.1 mm, and even smaller than 0.07 mm depending on the area of use.

There exist various possibilities of improving and further developing the teaching of the present invention. To this end, one may refer to the following description of a preferred embodiment of the invention with reference to the drawing. Also, in conjunction with the description of the preferred embodiment, generally preferred embodiments and further developments of the teaching are described in greater detail.

DETAILED DESCRIPTION OF THE PREFERRED EMBODIMENTS

Figure 1:
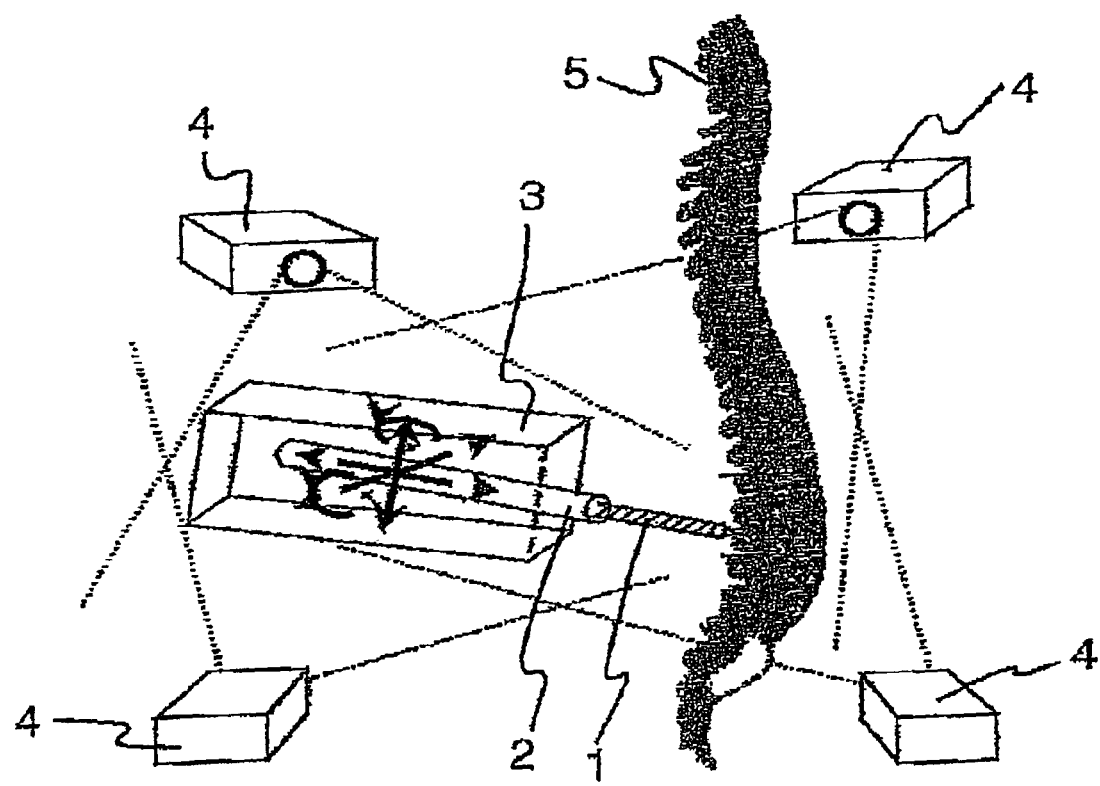
FIG. 1 is a schematic view of an embodiment of a device according to the invention for treating all types of body parts, in particular bones, organs, etc. of the human/animal body.

The embodiment of a device according to the invention as schematically illustrated in FIG. 1 comprises a tool 1 in the form of a drill, which is clamped into a tool holding fixture 2. By means of an actuation unit not shown in FIG. 1, it is possible to move the drill 1 relative to a housing 3 in six degrees of freedom: displacements along three Cartesian axes x, y, and z, as well as rotations about the three axes, with the displacement in the z direction being the advance of the drill, and the rotation about the z axis the rotation of the drill.

An optical position finding system detects the objects of interest. The objects being detected are the drill 1, and/or the housing 3, as well as a body part being treated, which is shown in FIG. 1 in the form of a spinal column 5. The images of cameras 4 are analyzed in a PC. By means of a stereoscopic rear projection, it is possible to determine from the camera images the position of the objects in the space.

Figure 2:
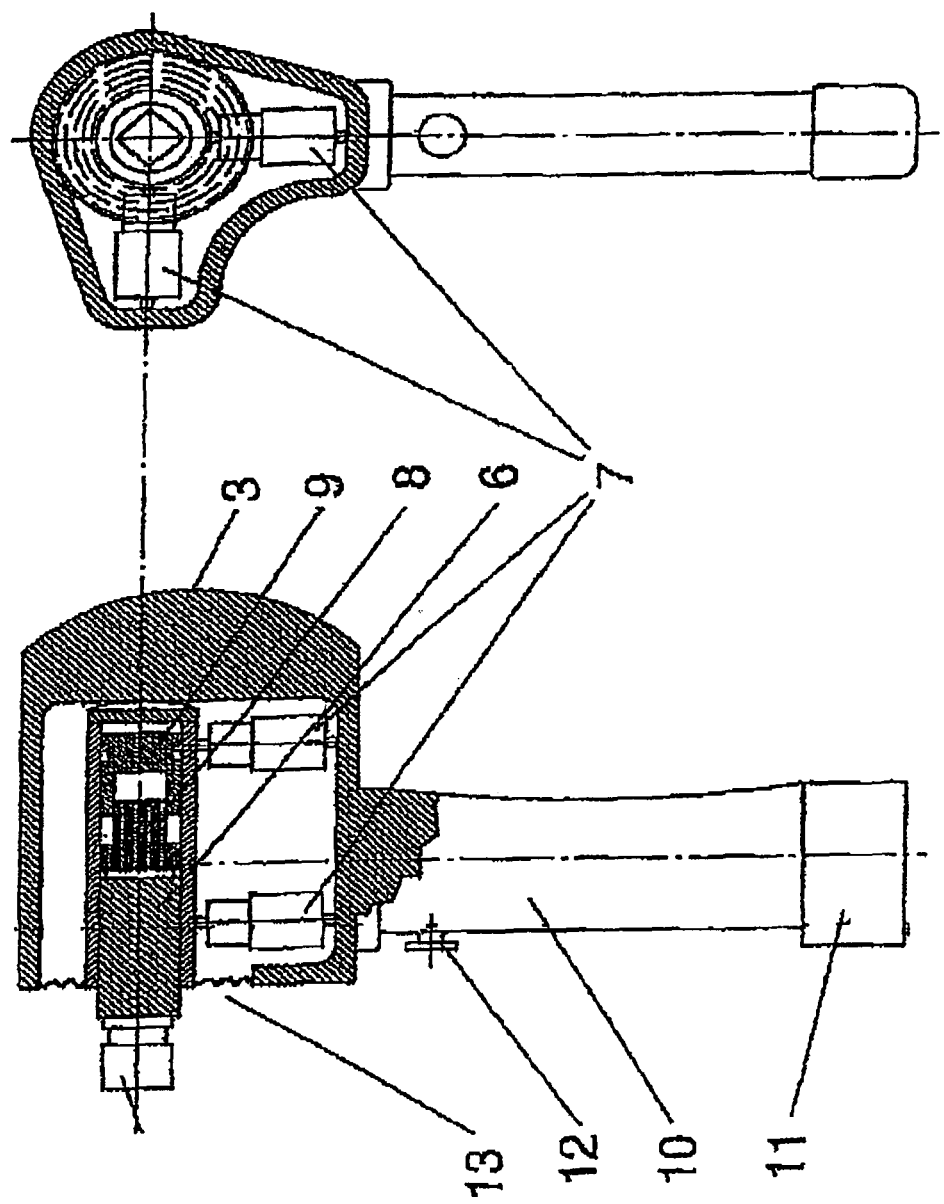
FIG. 2 is a schematic front and side view of an embodiment of a handheld appliance of the device according to the invention.

FIG. 2 schematically illustrates a front and a side view of an embodiment of a handheld appliance of the device according to the invention. A housing 3 accommodates a support 6, whose front end mounts a tool holding fixture 2 for receiving different tools in an exchangeable manner. The support 6 comprises an electrically controlled shaft of rotation for driving the tool, for example, a drill. Between the support 6 and the housing 3, linear actuators 7 are operative, which are able to move the support 6 and with it the drill within a predetermined work area and to any desired relative position with respect to the housing 3. The advance of the tool is produced via an electrically controlled z axis shaft 8 that extends on the axis of the drill behind the support 6. In addition, a pneumatic impact unit 9 is provided, so that the appliance can be used in a flexible manner for working parts of different quality, in particular different hardness.

The housing 3 is provided with a handle 10, which includes at its end facing away from the housing 3 a counterweight 11 for compensating the weight of the actuation unit. The handle 10 mounts an actuation switch 12, which allows the user to interrupt the procedure or also continue it by hand. The housing opening, through which the support 6 extends, is closed with a sealing diaphragm 13 for protecting the actuation unit and the internal sensory system against damage and soiling.

Figure 3:
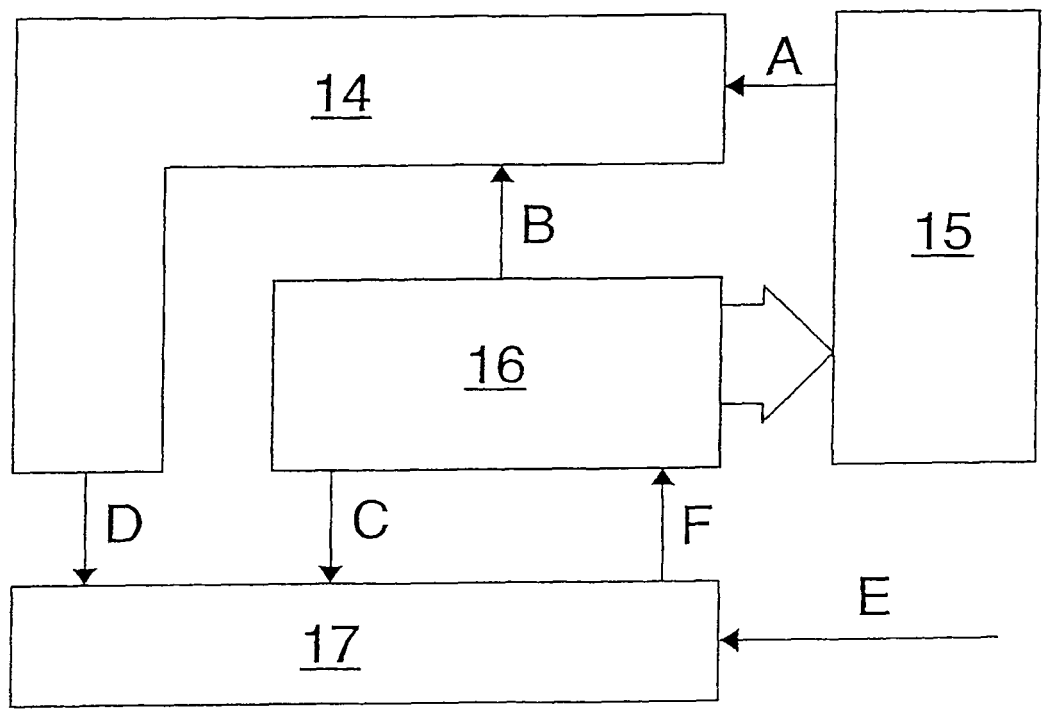
FIG. 3 is a schematic block diagram of the interaction of the individual components of the device according to the invention.

FIG. 3 schematically illustrates the interaction of the individual components of a device according to the invention. A position finding system 14 detects at a certain sampling rate the actual coordinates A of a patient 15, or quite generally of a body part being treated, and the actual coordinates B of the handheld appliance 16, or more specifically the actual coordinates of the tool. To this end, the corresponding positions that are to be detected are identified, for example, in the way of the aforesaid Application DE 102 25 007.4. In this process, the actual position of the tool can be determined directly, or the actual position of the housing is determined via the position finding system 14. An additional sensor not shown in FIG. 2 measures the relative position C of the drill in the coordinate system of the housing.

Both the relative position C and the relative position D of the housing 3 in the patient specific coordinate system are transmitted for evaluation to an adaptive and quick acting controller unit 17. Same compares the actual position data with the desired position data E from the (presurgical) operation planning, and generates a controlled variable F for a likewise not shown actuation unit. The actuation unit comprises actuators and moves the tool to the desired position regardless of the movement of the operator and the patient 15.

As regards further advantageous improvements and further developments of the teaching, the general part of the description on the one hand and the attached claims on the other hand are herewith incorporated by reference.

Finally, it should be especially emphasized that the above, merely arbitrarily selected embodiment serves only to explain the teaching of the invention, without however limiting it to the described embodiment.

The invention claimed is:

1. A device for manually treating body parts, such as parts of a human or animal body, comprising:
   a manually operable hand-held housing,
   a tool mounted for movement within the housing,
      at least two detectable markers, at least a first of said at least two detectable markers being associated with the tool and at least a second of said at least two detectable markers being associated with the body part being treated,
      a position finding system for detecting the positions of the tool and the body part being treated based on the at least two detectable markers, and
      an actuation unit causing relative movement between the tool and the housing and wherein when the positions of the tool and the body part being treated are detected by the position finding system, the actuation unit moves the tool within a predetermined work area to a predetermined relative position with respect to the body part being treated, while taking into account movements of both the housing and the body part being treated as detected by the position finding system,
      wherein the actuation unit is disposed within the housing and comprises an adaptive controller unit that evaluates position data based upon said at least two detectable markers and received from the position finding system and generates control signals to at least one actuator positioned between the tool and the housing.

2. The device of claim 1, wherein the actuation unit is configured for the detection of the positions of the tool and the body part being treated, and such that activation of the actuation unit can be performed continuously or repetitively.

3. The device of claim 1, wherein the tool is mounted in the housing to permit movement relative to the housing in a plurality of degrees of freedom.

4. The device of claim 1, wherein the housing is constructed to include a handle or pistol grip.

5. The device of claim 1, wherein the position finding system is constructed as an external optical, or acoustical, or magnetic, or mechanical, or radioactive system.

6. The device of claim 1, further comprising at least one detectable marker associated to the housing.

7. The device of claim 1, wherein the actuation unit comprises at least one sensor which is directly or indirectly associated to the housing and/or the tool for determining the relative position between the housing and the tool.

8. The device of claim 7, wherein the at least one sensor is a mechanical displacement sensor, or an inductive displacement sensor, or an angle sensor.

9. The device of claim 1, wherein the actuation unit comprises a plurality of actuators.

10. The device of claim 9, wherein within the work area, the actuators apply in each spatial direction forces of as high as 20 N.

11. The device of claim 1, further comprising means for monitoring the occurring forces and moments.

12. The device of claim 1, wherein the actuation unit comprises a hexapod robot.

13. The device of claim 1, wherein the actuation unit comprises a double epicyclical gear train.

14. The device of claim 1, wherein the tool comprises a drill, or a milling cutter, or a forceps, or a needle.

15. The device of claim 1, wherein the tool has a cylindrical work area of about 40 mm in diameter and about 40 mm in length.

16. The device of claim 1, wherein the actuation unit is configured to provide an accuracy of the position control of the tool which is ±0.1 mm in the Cartesian axes and ±0.1° in the rotational axes.

17. The device of claim 1 wherein the tool comprises a drill and the actuation unit is configured to rotate the drill about its axis.

18. The device of claim 17 wherein the actuation unit is configured to automatically rotate the drill about its axis when the actuation unit moves the drill to the predetermined relative position.

19. The device of claim 18 further comprising an acoustic or optical signal system configured to detect the predetermined relative position.

20. The device of claim 17 wherein the actuation unit is configured to automatically monitor a rate of advance, a force of advance, and a rotation speed of the drill.

21. The device of claim 17 wherein the actuation unit is configured to automatically stop rotation of the drill when the actuation unit moves the drill to a planned depth in the body part being treated.

* * * * *